(12) United States Patent
Tanaka et al.

(10) Patent No.: US 7,659,426 B2
(45) Date of Patent: Feb. 9, 2010

(54) TARGET PROTEIN OF ANTICANCER AGENT AND NOVEL ANTICANCER AGENT (SPNAL) CORRESPONDING THERETO

(75) Inventors: Akito Tanaka, Tsukuba (JP); Akira Yamazaki, Suita (JP); Takeshi Tsutsumi, Osaka (JP); Tomohiro Terada, Tsukuba (JP); Masayuki Haramura, Kamakura (JP)

(73) Assignee: Reverse Proteomics Research Institute Co., Ltd. (JP)

( * ) Notice: Subject to any disclaimer, the term of this patent is extended or adjusted under 35 U.S.C. 154(b) by 175 days.

(21) Appl. No.: 10/573,166

(22) PCT Filed: Nov. 30, 2004

(86) PCT No.: PCT/JP2004/018108

§ 371 (c)(1),
(2), (4) Date: Dec. 20, 2006

(87) PCT Pub. No.: WO2005/054181

PCT Pub. Date: Jun. 16, 2005

(65) Prior Publication Data

US 2007/0082955 A1    Apr. 12, 2007

(30) Foreign Application Priority Data

Dec. 1, 2003    (JP) .............................. 2003-401132

(51) Int. Cl.
*A01N 41/10*    (2006.01)
(52) U.S. Cl. .............................. 562/29; 562/30; 562/37; 562/58; 562/88; 514/708; 514/709
(58) Field of Classification Search ........................ None
See application file for complete search history.

(56) References Cited

U.S. PATENT DOCUMENTS 3,654,349 A    4/1972    Shen et al.
3,692,651 A    9/1972    Sletzinger et al.
5,466,823 A    11/1995   Talley et al.
5,756,529 A    5/1998    Isakson et al.
6,200,771 B1   3/2001    Liu et al.
6,500,610 B1   12/2002   Pamukcu et al.

FOREIGN PATENT DOCUMENTS

| JP | 53-12512 | 5/1978 |
|---|---|---|
| JP | 57-27107 | 6/1982 |
| JP | 9-506350 | 6/1997 |
| JP | 11-94823 | 4/1999 |
| JP | 11-514991 | 12/1999 |
| JP | 2000-186047 | 7/2000 |

OTHER PUBLICATIONS

Sherman et al Cancer Research vol. 43 p. 4283 (1983).*
Rehbein et al Journal of Neurochemistry vol. 82 p. 1039 (2002).*
Min et al Genes and Development vol. 11 p. 1023 (1997).*
Piazza et al., "Apoptosis Primarily Accounts for the Growth-inhibitory Properties of Sunlindac Metabolites and Involves a Mechanism That Is Independent of Cyclooxygenase Inhibition, Cell Cycle Arrest, and p53 Induction," *Cancer Research*, 57: 2452-2459 (1997).
Piazza et al., "Sulindac Sulfone Inhibits Azoxymethane-induced Colon Carcinogenesis in Rats without Reducing Prostaglandin Levels," *Cancer Research*, 57: 2909-2915 (1997).

* cited by examiner

*Primary Examiner*—Sheela J Huff
(74) *Attorney, Agent, or Firm*—Barnes & Thornburg LLP; Sandil K. Devadas

(57) ABSTRACT

The present invention provides a pharmaceutical composition containing, as an active ingredient, a compound that specifically binds to KSRP or a functional fragment thereof, and a screening method for the compound. KSRP is a novel target protein for anticancer agents; a compound capable of regulating the expression and activity of such a protein and a pharmaceutical composition containing it are highly useful for proliferative diseases, particularly as anticancer agents. By providing the novel target protein, the mechanism behind the anticancer effect that has conventionally been unexplainable can be elucidated.

9 Claims, 1 Drawing Sheet

SEQUENCE LISTING

```
<160> NUMBER OF SEQ ID NOS: 3

<210> SEQ ID NO 1
<211> LENGTH: 3009
<212> TYPE: DNA
<213> ORGANISM: Homo sapiens
<220> FEATURE:
<221> NAME/KEY: CDS
```

-continued

<222> LOCATION: (94)..(2229)
<223> OTHER INFORMATION:

<400> SEQUENCE: 1

```
tgtggagcga agccttgttc ccgcgttgag ccgccgccgc cgccgccgcc tcctcagctt      60
cagcctccgc gccaggcccg gccccgccgc gcc atg tcg gac tac agc acg gga     114
                                     Met Ser Asp Tyr Ser Thr Gly
                                       1               5 gga ccc ccg ccc ggg ccg ccg ccc gcc ggc ggg ggc ggg gga gcc          162
Gly Pro Pro Pro Gly Pro Pro Pro Ala Gly Gly Gly Gly Gly Ala
         10                  15                  20 gga ggc gcc ggg gga ggc cct ccg ccg ggc ccg cca ggc gcg ggg gac      210
Gly Gly Ala Gly Gly Gly Pro Pro Pro Gly Pro Pro Gly Ala Gly Asp
 25                  30                  35 cgg ggc ggc ggc ggt ccc tgc ggc ggc ggc ccg ggc ggg ggg tcg gcc      258
Arg Gly Gly Gly Gly Pro Cys Gly Gly Gly Pro Gly Gly Gly Ser Ala
 40                  45                  50                  55 ggg ggc ccc tct cag cca ccc ggc gga ggc ggc ccg gga atc cgc aag      306
Gly Gly Pro Ser Gln Pro Pro Gly Gly Gly Gly Pro Gly Ile Arg Lys
                 60                  65                  70 gac gct ttc gcc gac gcc gtg cag cgg gcc cgc cag att gca gcc aaa      354
Asp Ala Phe Ala Asp Ala Val Gln Arg Ala Arg Gln Ile Ala Ala Lys
             75                  80                  85 att gga ggc gat gct gcc acg aca gtg aat aac agc act cct gat ttt      402
Ile Gly Gly Asp Ala Ala Thr Thr Val Asn Asn Ser Thr Pro Asp Phe
         90                  95                 100 ggt ttt ggg ggc caa aag aga cag ttg gaa gat gga gat caa ccg gag      450
Gly Phe Gly Gly Gln Lys Arg Gln Leu Glu Asp Gly Asp Gln Pro Glu
     105                 110                 115 agc aag aag ctg gct tcc cag gga gac tca atc agt tct caa ctt gga      498
Ser Lys Lys Leu Ala Ser Gln Gly Asp Ser Ile Ser Ser Gln Leu Gly
120                 125                 130                 135 ccc atc cat cct ccc cca agg act tca atg aca gaa gag tac agg gtc      546
Pro Ile His Pro Pro Pro Arg Thr Ser Met Thr Glu Glu Tyr Arg Val
                140                 145                 150 cca gac ggc atg gtg ggc ctg atc att ggc aga gga ggt gaa caa att      594
Pro Asp Gly Met Val Gly Leu Ile Ile Gly Arg Gly Gly Glu Gln Ile
            155                 160                 165 aac aaa atc caa cag gat tca ggc tgc aaa gta cag att tct cca gac      642
Asn Lys Ile Gln Gln Asp Ser Gly Cys Lys Val Gln Ile Ser Pro Asp
        170                 175                 180 agc ggt ggc cta ccc gag cgc agt gtg tcc ttg aca gga gcc cca gaa      690
Ser Gly Gly Leu Pro Glu Arg Ser Val Ser Leu Thr Gly Ala Pro Glu
    185                 190                 195 tct gtc cag aaa gcc aag atg atg ctg gat gac att gtg tct cgg ggt      738
Ser Val Gln Lys Ala Lys Met Met Leu Asp Asp Ile Val Ser Arg Gly
200                 205                 210                 215 cgt ggg ggc ccc cca gga cag ttc cac gac aac gcc aac ggg ggc cag      786
Arg Gly Gly Pro Pro Gly Gln Phe His Asp Asn Ala Asn Gly Gly Gln
                220                 225                 230 aac ggc acc gtg cag gag atc atg atc ccc gcg ggc aag gcc ggc ctg      834
Asn Gly Thr Val Gln Glu Ile Met Ile Pro Ala Gly Lys Ala Gly Leu
            235                 240                 245 gtc att ggc aag ggc ggg gag acc att aag cag ctg cag gaa cgc gct      882
Val Ile Gly Lys Gly Gly Glu Thr Ile Lys Gln Leu Gln Glu Arg Ala
        250                 255                 260 gga gtg aag atg atc tta att cag gac gga tct cag aat acg aat gtg      930
Gly Val Lys Met Ile Leu Ile Gln Asp Gly Ser Gln Asn Thr Asn Val
    265                 270                 275
```

```
gac aaa cct ctc cgc atc att ggg gat cct tac aaa gtg cag caa gcc      978
Asp Lys Pro Leu Arg Ile Ile Gly Asp Pro Tyr Lys Val Gln Gln Ala
280                 285                 290                 295 tgt gag atg gtg atg gac atc ctc cgg gaa cgt gac caa ggc ggc ttt     1026
Cys Glu Met Val Met Asp Ile Leu Arg Glu Arg Asp Gln Gly Gly Phe
                300                 305                 310 ggg gac cgg aat gag tac gga tct cgg att ggc gga ggc atc gat gtg     1074
Gly Asp Arg Asn Glu Tyr Gly Ser Arg Ile Gly Gly Gly Ile Asp Val
            315                 320                 325 cca gtg ccc agg cat tct gtt ggc gtg gtc att ggc cgg agt gga gag     1122
Pro Val Pro Arg His Ser Val Gly Val Val Ile Gly Arg Ser Gly Glu
        330                 335                 340 atg atc aag aag atc cag aat gat gct ggc gtg cgg ata cag ttc aag     1170
Met Ile Lys Lys Ile Gln Asn Asp Ala Gly Val Arg Ile Gln Phe Lys
    345                 350                 355 caa gat gac ggg aca ggg ccc gag aag att gct cat ata atg ggg ccc     1218
Gln Asp Asp Gly Thr Gly Pro Glu Lys Ile Ala His Ile Met Gly Pro
360                 365                 370                 375 cca gac agg tgc gag cac gca gcc cgg atc atc aac gac ctc ctc cag     1266
Pro Asp Arg Cys Glu His Ala Ala Arg Ile Ile Asn Asp Leu Leu Gln
                380                 385                 390 agc ctc agg agt ggt ccc cca ggt cct cca ggg ggt cca ggc atg ccc     1314
Ser Leu Arg Ser Gly Pro Pro Gly Pro Pro Gly Gly Pro Gly Met Pro
            395                 400                 405 ccg ggg ggc cga ggc cga gga aga ggc caa ggc aat tgg ggt ccc cct     1362
Pro Gly Gly Arg Gly Arg Gly Arg Gly Gln Gly Asn Trp Gly Pro Pro
        410                 415                 420 ggc ggg gag atg acc ttc tcc atc ccc act cac aag tgt ggg ctg gtc     1410
Gly Gly Glu Met Thr Phe Ser Ile Pro Thr His Lys Cys Gly Leu Val
    425                 430                 435 atc ggc cga ggt ggc gag aat gtg aaa gcc ata aac cag cag acg gga     1458
Ile Gly Arg Gly Gly Glu Asn Val Lys Ala Ile Asn Gln Gln Thr Gly
440                 445                 450                 455 gcc ttc gta gag atc tcc cgg cag ctg cca ccc aac ggg gac ccc aac     1506
Ala Phe Val Glu Ile Ser Arg Gln Leu Pro Pro Asn Gly Asp Pro Asn
                460                 465                 470 ttc aag ttg ttc atc atc cgg ggt tca ccc cag cag att gac cac gcc     1554
Phe Lys Leu Phe Ile Ile Arg Gly Ser Pro Gln Gln Ile Asp His Ala
            475                 480                 485 aag cag ctt atc gag gaa aag atc gag ggt cct ctc tgc cca gtt gga     1602
Lys Gln Leu Ile Glu Glu Lys Ile Glu Gly Pro Leu Cys Pro Val Gly
        490                 495                 500 cca ggc cca ggt ggc cca ggc cct gct ggc cca atg ggg ccc ttc aat     1650
Pro Gly Pro Gly Gly Pro Gly Pro Ala Gly Pro Met Gly Pro Phe Asn
    505                 510                 515 cct ggg ccc ttc aac cag ggg cca ccc ggg gct ccc cca cat gcc ggg     1698
Pro Gly Pro Phe Asn Gln Gly Pro Pro Gly Ala Pro Pro His Ala Gly
520                 525                 530                 535 ggg ccc cct cct cac cag tac cca ccc cag ggc tgg ggc aat acc tac     1746
Gly Pro Pro Pro His Gln Tyr Pro Pro Gln Gly Trp Gly Asn Thr Tyr
                540                 545                 550 ccc cag tgg cag ccg cct gct cct cat gac cca agc aaa gca gct gca     1794
Pro Gln Trp Gln Pro Pro Ala Pro His Asp Pro Ser Lys Ala Ala Ala
            555                 560                 565 gcg gcc gcg gac ccc aac gcc gcg tgg gcc gcc tac tac tca cac tac     1842
Ala Ala Ala Asp Pro Asn Ala Ala Trp Ala Ala Tyr Tyr Ser His Tyr
        570                 575                 580 tac cag cag ccc ccg ggc ccc gtc ccc ggc ccc gca ccg gcc cct gcg     1890
Tyr Gln Gln Pro Pro Gly Pro Val Pro Gly Pro Ala Pro Ala Pro Ala
    585                 590                 595
```

```
gcc cca ccg gct cag ggt gag ccc cct cag ccc cca ccc acc ggc cag      1938
Ala Pro Pro Ala Gln Gly Glu Pro Pro Gln Pro Pro Pro Thr Gly Gln
600             605                 610                 615 tcg gac tac act aag gcc tgg gaa gag tat tac aaa aag atc ggc cag      1986
Ser Asp Tyr Thr Lys Ala Trp Glu Glu Tyr Tyr Lys Lys Ile Gly Gln
                620                 625                 630 cag ccc cag cag ccc gga gcg ccc cca cag cag gac tac acg aag gct      2034
Gln Pro Gln Gln Pro Gly Ala Pro Pro Gln Gln Asp Tyr Thr Lys Ala
            635                 640                 645 tgg gag gag tac tac aag aag caa gcg caa gtg gcc acc gga ggg ggt      2082
Trp Glu Glu Tyr Tyr Lys Lys Gln Ala Gln Val Ala Thr Gly Gly Gly
        650                 655                 660 cca gga gct ccc cca ggc tcc cag cca gac tac agt gcc gcc tgg gcg      2130
Pro Gly Ala Pro Pro Gly Ser Gln Pro Asp Tyr Ser Ala Ala Trp Ala
665                 670                 675 gaa tat tac aga cag cag gcc gct tac tac gga cag acc cca ggt cct      2178
Glu Tyr Tyr Arg Gln Gln Ala Ala Tyr Tyr Gly Gln Thr Pro Gly Pro
680                 685                 690                 695 ggc ggc ccc cag ccg ccg ccc acg cag cag gga cag cag cag gct caa      2226
Gly Gly Pro Gln Pro Pro Pro Thr Gln Gln Gly Gln Gln Gln Ala Gln
                700                 705                 710 tga atcgaatgaa tgtgaacttc ttcatctgtg aaaaatcttt ttttttttcca          2279 ttttgttctg tttgggggct tctgttttgt ttggcgagag agcgatggtg ccgtggggag    2339
tactggggag ccctcgcggc aagcagggtg ggggggactt ggggggcatgc cgggccctca   2399 ctctctcgcc tgttctgtgt ctcacatgct ttttctttca aaattgggat ccttccatgt    2459
tgagccagcc agagaagata gcgagatcta aatctctgcc aaaaaaaaaa aaaacttaaa   2519
aattaaaaac acaagagca aagcagaact tataaaatta tatatatata tattaaaaag    2579
tctctattct tcacccccca gccttcctga acctgcctct ctgaggataa agcaattcat    2639
tttctcccac cctcggccct cttgttttta aaataaactt ttaaaaagga aaaaaaaag    2699 tcactcttgc tatttctttt ttttagttag aggtggaaca ttccttggac caggtgttgt    2759
attgcaggac cccttccccc agcagccaag ccccctcttc tctccctccc gccctggctc    2819
agctcccgcg gccccgcccg tcccccctcc caggactggt ctgttgtctt ttcatctgtt   2879
caagaggaga ttgaaactga aaacaaaatg agaacaacaa aaaaaattgt atggcagttt    2939
ttacttttta tcgctcgttt ttaacttcac aaataaatga taacaaaacc tcaaaaaaaa   2999
aaaaaaaaaa                                                          3009

<210> SEQ ID NO 2
<211> LENGTH: 711
<212> TYPE: PRT
<213> ORGANISM: Homo sapiens

<400> SEQUENCE: 2

Met Ser Asp Tyr Ser Thr Gly Gly Pro Pro Pro Gly Pro Pro Pro Pro
1               5                   10                  15

Ala Gly Gly Gly Gly Ala Gly Gly Ala Gly Gly Pro Pro Pro
            20                  25                  30

Gly Pro Pro Gly Ala Gly Asp Arg Gly Gly Gly Pro Cys Gly Gly
            35                  40                  45

Gly Pro Gly Gly Gly Ser Ala Gly Pro Ser Gln Pro Gly Gly
        50                  55                  60

Gly Gly Pro Gly Ile Arg Lys Asp Ala Phe Ala Asp Ala Val Gln Arg
65                  70                  75                  80
```

-continued

```
Ala Arg Gln Ile Ala Ala Lys Ile Gly Gly Asp Ala Thr Thr Val
                 85                  90                  95
Asn Asn Ser Thr Pro Asp Phe Gly Phe Gly Gln Lys Arg Gln Leu
            100                 105                 110
Glu Asp Gly Asp Gln Pro Glu Ser Lys Lys Leu Ala Ser Gln Gly Asp
        115                 120                 125
Ser Ile Ser Ser Gln Leu Gly Pro Ile His Pro Pro Arg Thr Ser
    130                 135                 140
Met Thr Glu Glu Tyr Arg Val Pro Asp Gly Met Val Gly Leu Ile Ile
145                 150                 155                 160
Gly Arg Gly Gly Glu Gln Ile Asn Lys Ile Gln Gln Asp Ser Gly Cys
                165                 170                 175
Lys Val Gln Ile Ser Pro Asp Ser Gly Leu Pro Glu Arg Ser Val
            180                 185                 190
Ser Leu Thr Gly Ala Pro Glu Ser Val Gln Lys Ala Lys Met Met Leu
        195                 200                 205
Asp Asp Ile Val Ser Arg Gly Arg Gly Gly Pro Pro Gly Gln Phe His
    210                 215                 220
Asp Asn Ala Asn Gly Gly Gln Asn Gly Thr Val Gln Glu Ile Met Ile
225                 230                 235                 240
Pro Ala Gly Lys Ala Gly Leu Val Ile Gly Lys Gly Gly Glu Thr Ile
                245                 250                 255
Lys Gln Leu Gln Glu Arg Ala Gly Val Lys Met Ile Leu Ile Gln Asp
            260                 265                 270
Gly Ser Gln Asn Thr Asn Val Asp Lys Pro Leu Arg Ile Ile Gly Asp
        275                 280                 285
Pro Tyr Lys Val Gln Gln Ala Cys Glu Met Val Met Asp Ile Leu Arg
    290                 295                 300
Glu Arg Asp Gln Gly Gly Phe Gly Asp Arg Asn Glu Tyr Gly Ser Arg
305                 310                 315                 320
Ile Gly Gly Gly Ile Asp Val Pro Val Pro Arg His Ser Val Gly Val
                325                 330                 335
Val Ile Gly Arg Ser Gly Glu Met Ile Lys Lys Ile Gln Asn Asp Ala
            340                 345                 350
Gly Val Arg Ile Gln Phe Lys Gln Asp Asp Gly Thr Gly Pro Glu Lys
        355                 360                 365
Ile Ala His Ile Met Gly Pro Pro Asp Arg Cys Glu His Ala Ala Arg
    370                 375                 380
Ile Ile Asn Asp Leu Leu Gln Ser Leu Arg Ser Gly Pro Pro Gly Pro
385                 390                 395                 400
Pro Gly Gly Pro Gly Met Pro Pro Gly Gly Arg Gly Arg Gly Arg Gly
                405                 410                 415
Gln Gly Asn Trp Gly Pro Pro Gly Gly Glu Met Thr Phe Ser Ile Pro
            420                 425                 430
Thr His Lys Cys Gly Leu Val Ile Gly Arg Gly Gly Glu Asn Val Lys
        435                 440                 445
Ala Ile Asn Gln Gln Thr Gly Ala Phe Val Glu Ile Ser Arg Gln Leu
    450                 455                 460
Pro Pro Asn Gly Asp Pro Asn Phe Lys Leu Phe Ile Ile Arg Gly Ser
465                 470                 475                 480
Pro Gln Gln Ile Asp His Ala Lys Gln Leu Ile Glu Glu Lys Ile Glu
                485                 490                 495
```

```
Gly Pro Leu Cys Pro Val Gly Pro Gly Pro Gly Pro Ala
            500             505             510

Gly Pro Met Gly Pro Phe Asn Pro Gly Pro Phe Asn Gln Gly Pro Pro
            515             520             525

Gly Ala Pro Pro His Ala Gly Gly Pro Pro His Gln Tyr Pro Pro
        530             535             540

Gln Gly Trp Gly Asn Thr Tyr Pro Gln Trp Gln Pro Ala Pro His
545             550             555             560

Asp Pro Ser Lys Ala Ala Ala Ala Ala Asp Pro Asn Ala Ala Trp
                565             570             575

Ala Ala Tyr Tyr Ser His Tyr Tyr Gln Gln Pro Pro Gly Pro Val Pro
            580             585             590

Gly Pro Ala Pro Ala Pro Ala Ala Pro Pro Ala Gln Gly Glu Pro Pro
            595             600             605

Gln Pro Pro Pro Thr Gly Gln Ser Asp Tyr Thr Lys Ala Trp Glu Glu
610             615             620

Tyr Tyr Lys Lys Ile Gly Gln Gln Pro Gln Gln Pro Gly Ala Pro Pro
625             630             635             640

Gln Gln Asp Tyr Thr Lys Ala Trp Glu Glu Tyr Tyr Lys Lys Gln Ala
            645             650             655

Gln Val Ala Thr Gly Gly Pro Gly Ala Pro Pro Gly Ser Gln Pro
            660             665             670

Asp Tyr Ser Ala Ala Trp Ala Glu Tyr Tyr Arg Gln Gln Ala Ala Tyr
            675             680             685

Tyr Gly Gln Thr Pro Gly Pro Gly Gly Pro Gln Pro Pro Thr Gln
            690             695             700

Gln Gly Gln Gln Gln Ala Gln
705             710

<210> SEQ ID NO 3
<211> LENGTH: 585
<212> TYPE: PRT
<213> ORGANISM: Homo sapiens

<400> SEQUENCE: 3

Gly Asp Ser Ile Ser Ser Gln Leu Gly Pro Ile His Pro Pro Arg
1               5               10              15

Thr Ser Met Thr Glu Glu Tyr Arg Val Pro Asp Gly Met Val Gly Leu
            20              25              30

Ile Ile Gly Arg Gly Gly Glu Gln Ile Asn Lys Ile Gln Gln Asp Ser
            35              40              45

Gly Cys Lys Val Gln Ile Ser Pro Asp Ser Gly Gly Leu Pro Glu Arg
        50              55              60

Ser Val Ser Leu Thr Gly Ala Pro Glu Ser Val Gln Lys Ala Lys Met
65              70              75              80

Met Leu Asp Asp Ile Val Ser Arg Gly Arg Gly Gly Pro Pro Gly Gln
            85              90              95

Phe His Asp Asn Ala Asn Gly Gly Gln Asn Gly Thr Val Gln Glu Ile
            100             105             110

Met Ile Pro Ala Gly Lys Ala Gly Leu Val Ile Gly Lys Gly Gly Glu
            115             120             125

Thr Ile Lys Gln Leu Gln Glu Arg Ala Gly Val Lys Met Ile Leu Ile
            130             135             140

Gln Asp Gly Ser Gln Asn Thr Asn Val Asp Lys Pro Leu Arg Ile Ile
145             150             155             160
```

-continued

```
Gly Asp Pro Tyr Lys Val Gln Ala Cys Glu Met Val Met Asp Ile
            165                 170                 175
Leu Arg Glu Arg Asp Gln Gly Gly Phe Gly Asp Arg Asn Glu Tyr Gly
            180                 185                 190
Ser Arg Ile Gly Gly Gly Ile Asp Val Pro Val Pro Arg His Ser Val
            195                 200                 205
Gly Val Val Ile Gly Arg Ser Gly Glu Met Ile Lys Lys Ile Gln Asn
    210                 215                 220
Asp Ala Gly Val Arg Ile Gln Phe Lys Gln Asp Asp Gly Thr Gly Pro
225                 230                 235                 240
Glu Lys Ile Ala His Ile Met Gly Pro Pro Asp Arg Cys Glu His Ala
                245                 250                 255
Ala Arg Ile Ile Asn Asp Leu Leu Gln Ser Leu Arg Ser Gly Pro Pro
            260                 265                 270
Gly Pro Pro Gly Gly Pro Gly Met Pro Pro Gly Gly Arg Gly Arg Gly
            275                 280                 285
Arg Gly Gln Gly Asn Trp Gly Pro Pro Gly Glu Met Thr Phe Ser
    290                 295                 300
Ile Pro Thr His Lys Cys Gly Leu Val Ile Gly Arg Gly Gly Glu Asn
305                 310                 315                 320
Val Lys Ala Ile Asn Gln Gln Thr Gly Ala Phe Val Glu Ile Ser Arg
                325                 330                 335
Gln Leu Pro Pro Asn Gly Asp Pro Asn Phe Lys Leu Phe Ile Ile Arg
            340                 345                 350
Gly Ser Pro Gln Gln Ile Asp His Ala Lys Gln Leu Ile Glu Glu Lys
            355                 360                 365
Ile Glu Gly Pro Leu Cys Pro Val Gly Pro Gly Pro Gly Gly Pro Gly
    370                 375                 380
Pro Ala Gly Pro Met Gly Pro Phe Asn Pro Gly Pro Phe Asn Gln Gly
385                 390                 395                 400
Pro Pro Gly Ala Pro Pro His Ala Gly Gly Pro Pro His Gln Tyr
                405                 410                 415
Pro Pro Gln Gly Trp Gly Asn Thr Tyr Pro Gln Trp Gln Pro Pro Ala
            420                 425                 430
Pro His Asp Pro Ser Lys Ala Ala Ala Ala Ala Asp Pro Asn Ala
            435                 440                 445
Ala Trp Ala Ala Tyr Tyr Ser His Tyr Tyr Gln Gln Pro Pro Gly Pro
    450                 455                 460
Val Pro Gly Pro Ala Pro Ala Pro Ala Ala Pro Ala Gln Gly Glu
465                 470                 475                 480
Pro Pro Gln Pro Pro Thr Gly Gln Ser Asp Tyr Thr Lys Ala Trp
                485                 490                 495
Glu Glu Tyr Tyr Lys Lys Ile Gly Gln Gln Pro Gln Pro Gly Ala
            500                 505                 510
Pro Pro Gln Gln Asp Tyr Thr Lys Ala Trp Glu Glu Tyr Tyr Lys Lys
            515                 520                 525
Gln Ala Gln Val Ala Thr Gly Gly Pro Gly Ala Pro Pro Gly Ser
    530                 535                 540
Gln Pro Asp Tyr Ser Ala Ala Trp Ala Glu Tyr Tyr Arg Gln Gln Ala
545                 550                 555                 560
```

```
Ala Tyr Tyr Gly Gln Thr Pro Gly Pro Gly Gly Pro Gln Pro Pro Pro
                565             570                 575
Thr Gln Gln Gly Gln Gln Gln Ala Gln
            580             585
```

TARGET PROTEIN OF ANTICANCER AGENT AND NOVEL ANTICANCER AGENT (SPNAL) CORRESPONDING THERETO

CROSS-REFERENCE TO RELATED APPLICATIONS

This application is a national phase of international patent application no. PCT/JP2004/018108, filed Nov. 30, 2004, which claims the benefit of patent application no. JP 2003-401132, filed Dec. 1, 2003, the entire content of which is incorporated herein by reference.

TECHNICAL FIELD

The present invention relates to a novel drug discovery target. More specifically, the present invention relates to a target molecule considered to account for the efficacy of non-steroidal anti-inflammatory drugs (NSAIDs) such as sulindac and derivatives thereof for familial adenomatous polyposis (FAP). The present invention also relates to a compound that specifically binds to the target molecule.

BACKGROUND OF THE INVENTION

As the base sequences of the human genomes have been decoded, research subjects have been shifted to genome drug discovery and the search and identification of drug discovery targets. Against this background, there are some noticeable reports that non-steroidal anti-inflammatory drugs (NSAIDs) such as sulindac, derivatives thereof, and celecoxib, which have traditionally been used as non-steroidal anti-inflammatory analgesics, also exhibit efficacy in the area of cancers such as familial adenomatous polyposis (FAP) that was not at all anticipated in early days, one of which concerns the identification of a target considered to account for the efficacy of these compounds in the cancer area.

To date, as the mechanism behind this phenomenon, mainly the contribution of cyclooxygenase (COX) (COX1, COX2), which is a specific target for these NSAIDs, has been suggested (see Cancer Research, 57, pp. 2452-2459 (1997)).

However, sulindac and certain sulindac derivatives (specifically sulindac sulfone) exhibit only weak inhibitory effect on COX1 and COX2 (see Cancer Research, 57, pp. 2909-2915 (1997)).

Regarding the efficacy for FAP of sulindac derivatives (sulindac sulfone and the like), which have weak activity on COX as described above, and whose involvement in anticancer effect is unlikely, their relation to phosphodiesterase 5 (PDE5) inhibitory effect has been suggested to date, and experiments have been performed at in vitro and in vivo laboratory levels (see Cancer Research, 57, pp. 2452-2459 (1997)). However, something remains insufficient to explain all the anticancer effect of these derivatives in clinical settings, and the elucidation of the true mechanism thereof has been awaited.

BRIEF SUMMARY OF THE INVENTION

An object of the present invention is to identify a target considered to account for the efficacy of NSAIDs such as sulindac, derivatives thereof and celecoxib for familial adenomatous polyposis, and provide a screening method for a compound useful in the treatment of diseases such as familial adenomatous polyposis using the target and a compound obtained by the screening.

With the aim of solving the above-described problems, the present inventors conducted diligent investigations in search of a target that permits an explanation of the mechanism behind the anticancer effect (clinical efficacy) of NSAIDs such as sulindac, derivatives thereof and celecoxib. As a result, the inventors found that a protein called KSRP (KH-type splicing regulatory protein), which regulates the splicing of mRNA, serves as a novel drug discovery target sufficient to explain the anticancer effect of these derivatives (Table 1), developed a screening method for a compound useful in the treatment of diseases such as proliferative diseases, inflammatory diseases and encephalopathies using such a target or cells that express the target, obtained a candidate compound, and developed the present invention.

TABLE 1

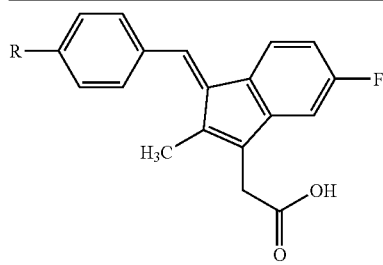

| | COX1 inhibitory effect | COX2 inhibitory effect | Status of development as anticancer agent | KSRP bindability |
|---|---|---|---|---|
| Sulindac sulfide (R = SCH$_3$) | ○ | ○ | No development | x |
| Sulindac (R = SOCH$_3$) | x | x | Under development for FAP | ○ |
| Sulindac sulfone (R = SO$_2$CH$_3$) | x | x | FAP (under application)/esophageal cancer/small-cell lung cancer (under development at P2 phase)/prostatic cancer/breast cancer/non-small- | ○ |

TABLE 1-continued

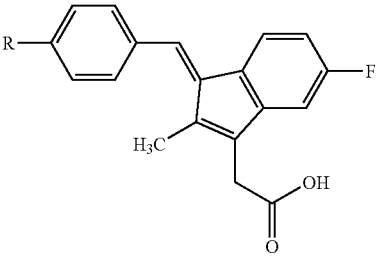

| | COX1 inhibitory effect | COX2 inhibitory effect | Status of development as anticancer agent | KSRP bindability |
|---|---|---|---|---|
| | | | cell cancer (under development at P3 phase) | | x: weak effect,
o: definite inhibitory effect

Accordingly, the present invention relates to the following:

[1] A compound represented by the formula (I) or the formula (II):

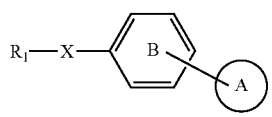 (I)

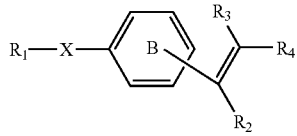 (II)

wherein X is;

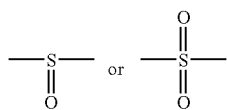

ring A is an optionally substituted saturated or unsaturated cyclic hydrocarbon group or saturated or unsaturated heterocyclic group;

ring B is a benzene ring optionally further having one to four substituents;

$R_1$ is an optionally substituted lower alkyl group, an optionally substituted aryl group, a substituted amido group or an optionally substituted amino group;

each of $R_2$ to $R_4$, whether identical or not, is a hydrogen atom, a saturated or unsaturated hydrocarbon group or a saturated or unsaturated heterocyclic group ($R_3$ and $R_4$ may bind together to form a ring)], except that the compounds shown below are excluded,

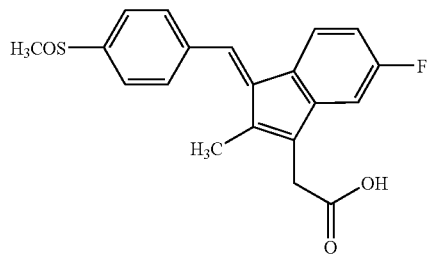

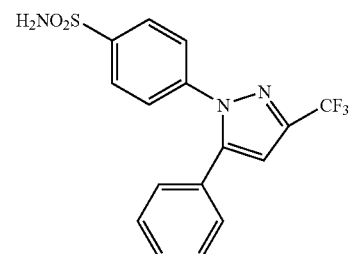

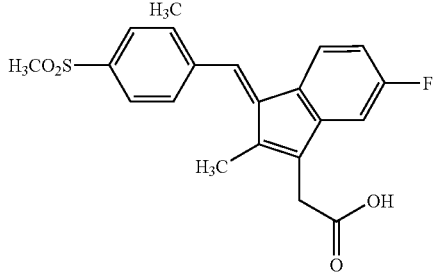

or a pharmaceutically acceptable salt thereof.

[2] The compound described in [1] above, wherein the compound represented by the formula (I) is a compound represented by the formula (I'):

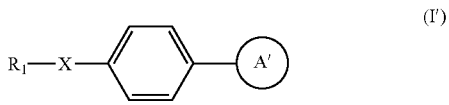 (I')

wherein ring A' is an optionally substituted saturated or unsaturated heterocyclic group; the other symbols have the same definitions as [1] above, or a pharmaceutically acceptable salt thereof.

[3] The compound described in [2] above, wherein in the formula (I'), the ring A' is a saturated or unsaturated cyclic hydrocarbon group or saturated or unsaturated heterocyclic group optionally substituted by at least one substituent selected from the group consisting of saturated or unsaturated cyclic hydrocarbon groups, saturated or unsaturated heterocyclic groups, carboxyl groups, substituted amido groups and optionally substituted lower alkyl groups, or a pharmaceutically acceptable salt thereof.

[4] The compound described in [2] above, wherein in the formula (I'), the ring A' is a saturated or unsaturated heterocyclic group having both any one substituent selected from the group consisting of saturated or unsaturated cyclic hydrocarbon groups and saturated or unsaturated heterocyclic groups, and any one substituent selected from the group consisting of carboxyl groups, substituted amido groups and optionally substituted lower alkyl groups, or a pharmaceutically acceptable salt thereof.

[5] The compound described in [1] above, wherein in the formula (II), the ring formed by mutually binding $R_3$ and $R_4$ is a saturated or unsaturated cyclic hydrocarbon group or saturated or unsaturated heterocyclic group optionally having at least one substituent selected from the group consisting of carboxyl groups, substituted amido groups and optionally substituted lower alkyl groups, or a pharmaceutically acceptable salt thereof.

[6] The compound described in [5] above, wherein in the formula (II), the ring formed by mutually binding $R_3$ and $R_4$ is a saturated or unsaturated cyclic hydrocarbon group optionally having at least one substituent selected from the group consisting of carboxyl groups, substituted amido groups and optionally substituted lower alkyl groups, or a pharmaceutically acceptable salt thereof.

[7] The compound described in [6] above, wherein the saturated or unsaturated cyclic hydrocarbon group is indene, or a pharmaceutically acceptable salt thereof.

[8] A pharmaceutical composition comprising, as an active ingredient, the compound described in any of [1] to [7] above or a pharmaceutically acceptable salt thereof.

[9] The pharmaceutical composition described in [8] above, which is for the treatment of a disease selected from the group consisting of a proliferative disease, an inflammatory disease and an encephalopathy.

[10] A pharmaceutical composition comprising, as an active ingredient, a compound that specifically binds to a protein having the amino acid sequence of SEQ ID NO:2.

[11] A pharmaceutical composition comprising, as an active ingredient, a compound that specifically binds to a protein having the amino acid sequence of SEQ ID NO:2, wherein one or more amino acids are deleted, substituted or added, and which;
(i) binds to a compound of formula 1, and
(ii) does not bind to a compound of formula 2.

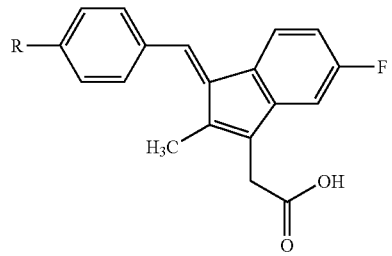

R=SOMe or SO$_2$Me

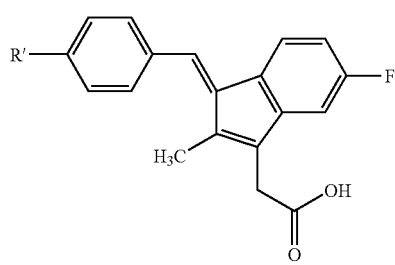

R'=SMe

[12] A pharmaceutical composition comprising, as an active ingredient, a compound that specifically binds to a protein having the amino acid sequence of SEQ ID NO:3.

[13] A pharmaceutical composition comprising, as an active ingredient, a compound that specifically binds to a protein having the amino acid sequence of SEQ ID NO:3, wherein one or more amino acids are deleted, substituted or added, and which;
(i) binds to a compound of formula 1, and
(ii) does not bind to a compound of formula 2,

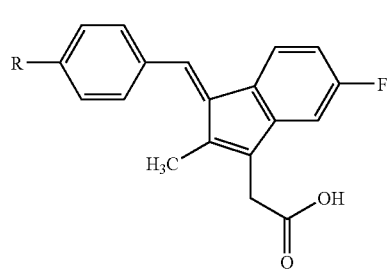

R=SOMe or SO$_2$Me

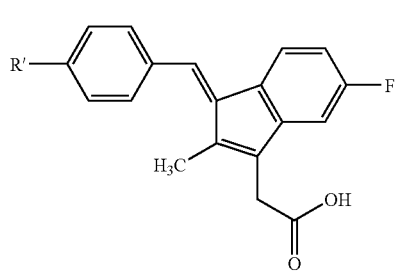

R'=SMe

[14] The pharmaceutical composition described in any of [10] to [13] above, which is for the treatment of a disease selected from the group consisting of a proliferative disease, an inflammatory disease and an encephalopathy.

[15] The pharmaceutical composition described in [14] above, wherein the proliferative disease is at least one kind selected from the group consisting of familial adenomatous polyposis, esophageal cancer, small-cell lung cancer, prostatic cancer, breast cancer, non-small-cell cancer and ovarian cancer.

[16] A pharmaceutical composition comprising, as an active ingredient, a compound that specifically binds to KSRP.

[17] A pharmaceutical composition comprising, as an active ingredient, a compound that regulates the expression of KSRP.

[18] A pharmaceutical composition comprising, as an active ingredient, a compound that regulates the activity of KSRP.

[19] The pharmaceutical composition described in any of [16] to [18] above, which is for the treatment of a disease selected from the group consisting of a proliferative disease, an inflammatory disease and an encephalopathy.

[20] The pharmaceutical composition described in [19] above, wherein the proliferative disease is at least one kind selected from the group consisting of familial adenomatous polyposis, esophageal cancer, small-cell lung cancer, prostatic cancer, breast cancer, non-small-cell cancer and ovarian cancer.

[21] A method for screening for a compound useful in the treatment of a disease selected from the group consisting of a proliferative disease, an inflammatory disease and an encephalopathy, which comprises the steps shown below;
(1) a step of bringing KSRP or a functional fragment thereof into contact with a test compound,
(2) a step of determining whether or not the test compound specifically binds to KSRP or a functional fragment thereof, and
(3) a step of selecting a test compound that specifically binds to KSRP or a functional fragment thereof in the step (2) above.

[22] A method for screening for a compound useful in the treatment of a disease selected from the group consisting of a proliferative disease, an inflammatory disease and an encephalopathy, which comprises the steps shown below;
(1) a step of bringing a protein having the amino acid sequence of SEQ ID NO:2 or a functional fragment thereof into contact with a test compound,
(2) a step of determining whether or not the test compound specifically binds to the protein or a functional fragment thereof, and
(3) a step of selecting a test compound that specifically binds to the protein or a functional fragment thereof in the step (2) above.

[23] A method for screening for a compound useful in the treatment of a disease selected from the group consisting of a proliferative disease, an inflammatory disease and an encephalopathy, which comprises the steps shown below;

(1) a step of bringing a protein having the amino acid sequence of SEQ ID NO:2, wherein one or more amino acids are deleted, substituted or added, and which:
(i) binds to a compound of formula 1, and
(ii) does not bind to a compound of formula 2

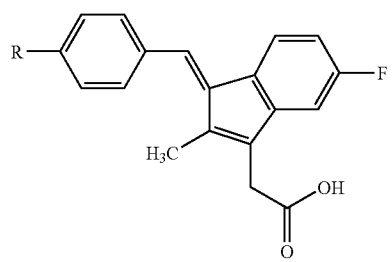

R=SOMe or SO$_2$Me

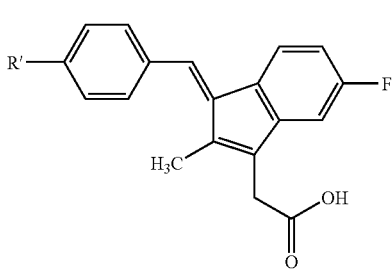

R'=SMe or a functional fragment thereof into contact with a test compound,
(2) a step of determining whether or not the test compound specifically binds to the protein or a functional fragment thereof, and
(3) a step of selecting a test compound that specifically binds to the protein or a functional fragment thereof in the step (2) above.

[24] A method for screening for a compound useful in the treatment of a disease selected from the group consisting of a proliferative disease, an inflammatory disease and an encephalopathy, which comprises the steps shown below;
(1) a step of bringing a protein having the amino acid sequence of SEQ ID NO:3 or a functional fragment thereof into contact with a test compound,
(2) a step of determining whether or not the test compound specifically binds to the protein or a functional fragment thereof, and
(3) a step of selecting a test compound that specifically binds to the protein or a functional fragment thereof in the step (2) above.

[25] A method for screening for a compound useful in the treatment of a disease selected from the group consisting of a proliferative disease, an inflammatory disease and an encephalopathy, which comprises the steps shown below;

(1) a step of bringing a protein having the amino acid sequence of SEQ ID NO:3, wherein one or more amino acids are deleted, substituted or added, and which:
(i) binds to a compound of formula 1, and
(ii) does not bind to a compound of formula 2

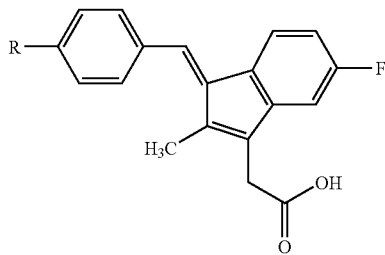

R=SOMe or SO₂Me

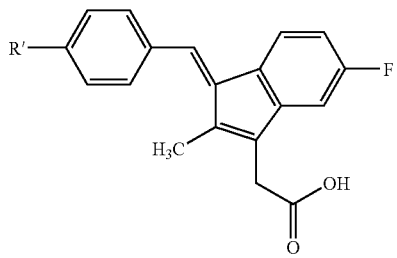

R'=SMe or a functional fragment thereof into contact with a test compound, (2) a step of determining whether or not the test compound specifically binds to the protein or a functional fragment thereof, and (3) a step of selecting a test compound that specifically binds to the protein or a functional fragment thereof in the step (2) above.

[26] A compound useful in the treatment of a disease selected from the group consisting of a proliferative disease, an inflammatory disease and an encephalopathy, obtained by the screening method described in any of [21] to [25] above.

DETAILED DESCRIPTION OF THE INVENTION

Figure 1:
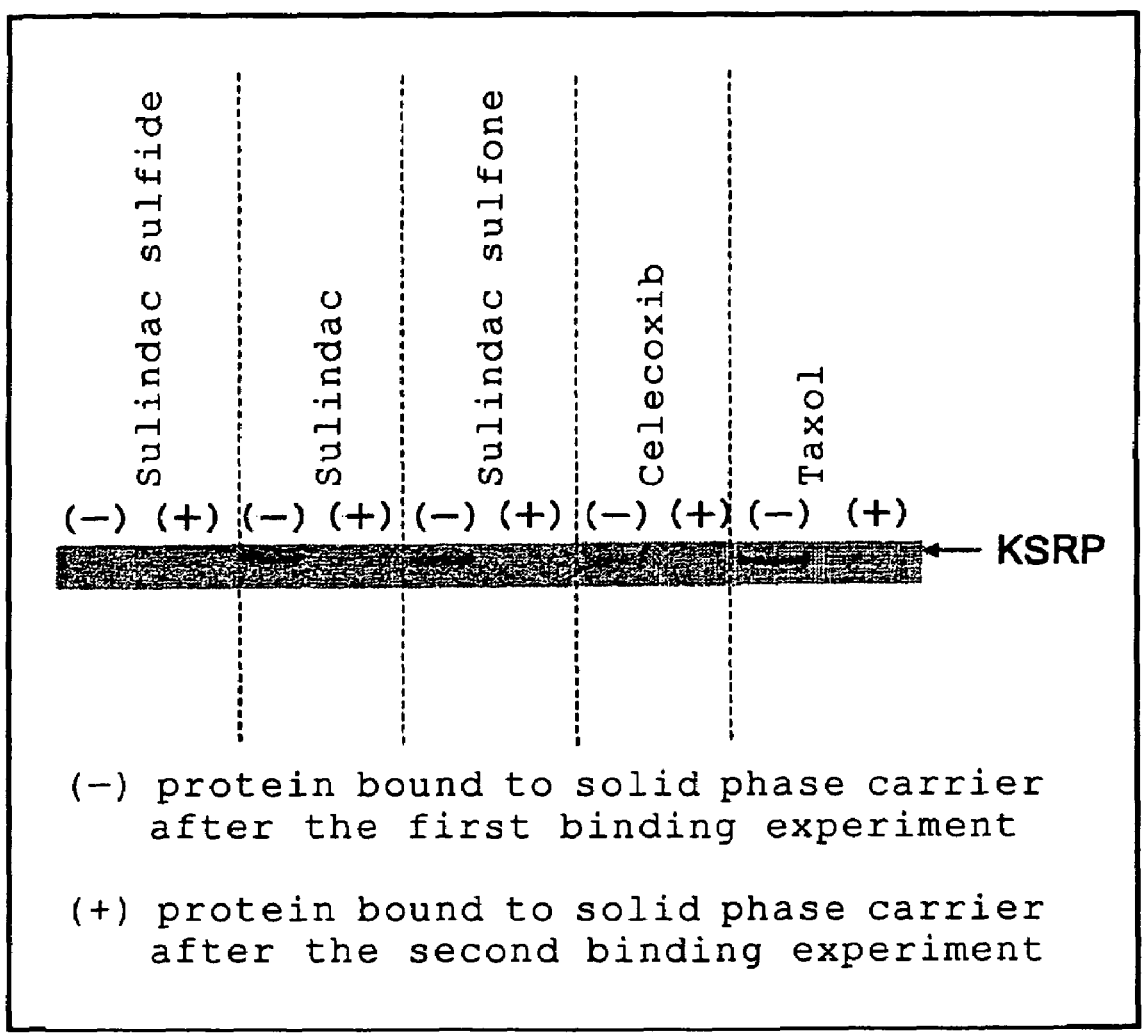
FIG. 1 shows the results of an examination of the specificity of each compound for KSRP binding. Onto the solid phase carrier wherein a compound that specifically binds to KSRP is immobilized, KSRP binds rapidly upon the first immobilized resin treatment. To the resins wherein four compounds were immobilized, other than the resin wherein sulindac sulfide was immobilized, KSRP bound.

KSRP (KH-type splicing regulatory protein), also referred to as FBP2 (FUSE binding protein 2), is a protein that was initially discovered as a protein similar to FBP (FUSE binding protein), which functions importantly in the expression of c-myc, by D. Levens at NIH in 1996 (J. Biol. Chem., 271(49), pp. 31679-31687 (1996)), and later discovered separately as a protein essential to the splicing variant maturation of c-src involved in proliferative effect by another group in 1997 (Gene & Development, 11, pp. 1023-1036 (1997)). Also, KSRP has recently been drawing attention as a protein identified as a substrate protein for caspase-3,7, which is important in inducing apoptosis to cells (Protein & Peptide Lett., 9(6), pp. 511-519 (2002)), and also identified as a protein that exhibits remarkable changes in proteome analysis in inducing apoptosis to Jurakat cells using the Fas antigen (J. Biol. Chem., 276(28), pp. 26044-26050 (2001)) and the like. More specifically, KSRP is a protein comprising 711 amino acids shown by the amino acid sequence of SEQ ID NO:2 (accession No. NP_003676).

The KSRP in the present invention need not always be shown solely by the amino acid sequence of SEQ ID NO:2, as long as it is a protein that:
(i) binds to a compound of formula 1, and
(ii) does not bind to a compound of formula 2

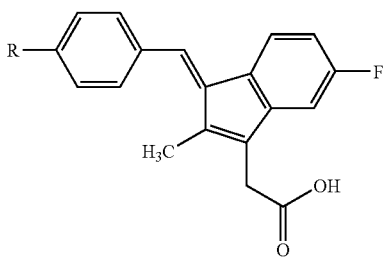

R=SOMe or SO₂Me

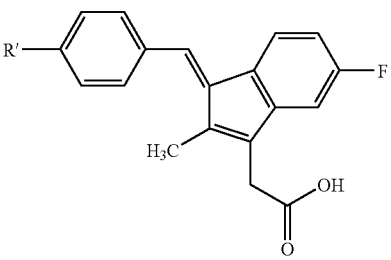

R'=SMe and it may be a protein having the amino acid sequence of SEQ ID NO:2 or a protein having the amino acid sequence of SEQ ID NO:2, wherein one or more amino acids are deleted, substituted or added. More specifically, the KSRP is a protein shown by an amino acid sequence having a homology of 60% or more, 70% or more, 80% or more, preferably 90% or more, and particularly preferably 95% or more, to the amino acid sequence of SEQ ID NO:2, and is further preferably a protein (polypeptide) comprising 40 continuous amino acids or more, preferably 70 amino acids or more, and particularly preferably 100 amino acids or more, in the amino acid sequence of SEQ ID NO:2. As used herein, "homology" means the extent of sequence correlation between two polypeptide sequences. Homology can easily be calculated. A large number of methods of measuring the homology between two polypeptide sequences are known, and the term "homology" (also called identity) is obvious to those skilled in the art. Ordinary methods used to measure the homology of two sequences include, but are not limited to, those disclosed in Martin, J. Bishop (Ed.), Guide to Huge Computers, Academic Press, San Diego (1994); Carillo, H. & Lipman, D., SIAM J. Applied Math., 48:1073 (1988) and the like. As a preferable method for measuring the homology, one designed to obtain the largest matching portion between the two sequences tested can be mentioned. As such a method, one assembled in a computer program can be mentioned. Preferable computer programming methods for measuring the homology between two sequences include, but are not limited to, the GCG program package (Devereux, J. et al., Nucleic Acids Research, 12(1):387 (1984)), BLASTP, FASTA and the like; methods known in the art can be used.

Furthermore, the KSRP in the present invention may be a fragment of KSRP, as long as it (i) binds to a compound of formula 1 and (ii) does not bind to a compound of formula 2, provided that is can serve as a target for a series of NSAIDs such as sulindac derivatives; such a fragment is hereinafter also referred to as a functional fragment of KSRP. As the functional fragment, specifically, a protein represented by the amino acid sequence of SEQ ID NO:3, a protein that still (i) binds to a compound of formula 1 and (ii) does not bind to a compound of formula 2, and that comprises the amino acid sequence of SEQ ID NO:3, wherein one or more amino acids are deleted, substituted or added, and the like can be mentioned.

All these modes are encompassed in the KSRP in the present invention unless otherwise stated.

To "specifically bind" is exemplified by the relation of a specific receptor to an agonist or an antagonist, the relation of an enzyme to a substrate, and the relation of, for example, an FK506-binding protein (target molecule) to FK506 (ligand), a steroid hormone receptor to a steroid hormone (e.g., dexamethasone and glucocorticoid receptor), HDAC to the anticancer agent trapoxin, and the like, and can be confirmed as numerical values of Kd, Ka and the like by competitive experiments and the like. As described in Examples below, this can also be confirmed by a visual means such as electrophoresis, in addition to representation by specific numerical values.

The present invention provides a pharmaceutical composition comprising, as an active ingredient, a compound that specifically binds to KSRP (a protein having the amino acid sequence of SEQ ID NO:2, a protein that has the amino acid sequence of SEQ ID NO:2, wherein one or more amino acids are deleted, substituted or added, and which (i) binds to a compound of formula 1 and (ii) does not bind to a compound of formula 2, and the like) and a functional fragment thereof (for example, a protein having the amino acid sequence of SEQ ID NO:3, a protein that has the amino acid sequence of SEQ ID NO:3, wherein one or more amino acids are deleted, substituted or added, and which (i) binds to a compound of formula 1 and (ii) does not bind to a compound of formula 2, and the like). Such a compound is capable of 5 regulating the expression of KSRP, and/or regulating the activity thereof, by binding to KSRP, which is a novel anticancer target, and is therefore useful in the prevention and treatment of various diseases mediated by KSRP. For example, Taxol, which has been reported to be applicable to ovarian cancer, non-small-cell cancer, breast cancer and the like, also binds to KSRP (see Examples below). Although as examples of the various diseases mediated by KSRP, proliferative diseases, inflammatory diseases, encephalopathies and the like can be mentioned from the existing reports described above, there is no report that KSRP is a target utilizable for screening of a compound useful in the treatment of such a disease. "A proliferative disease" is a disease characterized by abnormal proliferation of cells, which proliferation is considered to be associated with the onset of the disease and the progression of symptoms; for example, familial adenomatous polyposis, esophageal cancer, small-cell lung cancer, prostatic cancer, breast cancer, non-small-cell cancer and the like can be mentioned. "An inflammatory disease" is an exogenous or endogenous, acute or chronic disease, and, in the case of the acute disease, it is accompanied by the five cardinal signs of fever, reddening, swelling, pain and dysfunction. "An encephalopathy" means an exogenous or endogenous dysfunction observed in the brain.

Furthermore, according to the finding in the present invention that KSRP can serve as a novel drug discovery target for proliferative diseases, inflammatory diseases, encephalopathies and the like, a compound that does not bind directly to KSRP but directly or indirectly acts on KSRP to regulate the expression and activity of KSRP can also be described as being useful in the treatment of proliferative diseases, inflammatory diseases and encephalopathies.

As specific examples of the compound contained as an active ingredient in the present invention, a compound represented by the formula (I) or the formula (II):

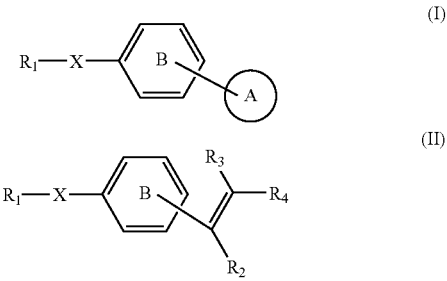

wherein X is;

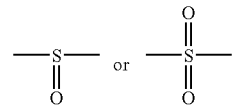

ring A is an optionally substituted saturated or unsaturated cyclic hydrocarbon group or saturated or unsaturated heterocyclic group;

ring B is a benzene ring optionally further having one to four substituents;

$R_1$ is an optionally substituted lower alkyl group, an optionally substituted aryl group, a substituted amido group or an optionally substituted amino group;

each of $R_2$ to $R_4$, whether identical or not, is a hydrogen atom, a saturated or unsaturated hydrocarbon group or a saturated or unsaturated heterocyclic group ($R_3$ and $R_4$ may bind together to form a ring)], except that the compounds shown below are excluded,

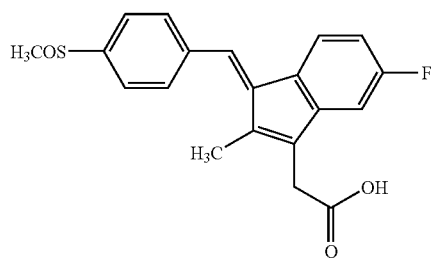

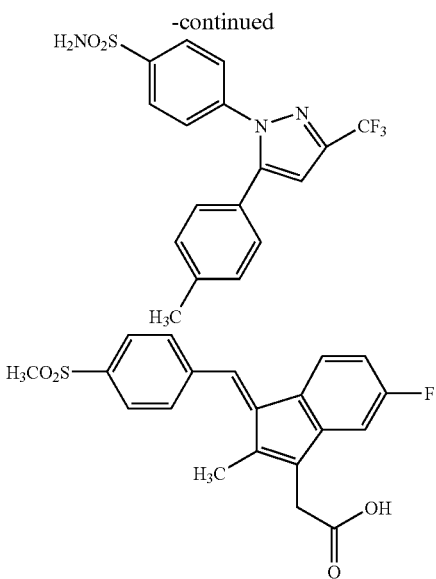

or a pharmaceutically acceptable salt thereof can be mentioned.

As used herein, "a saturated or unsaturated cyclic hydrocarbon group" is a saturated or unsaturated cyclic hydrocarbon group having 3 to 18 carbon atoms; specifically, for example, an alicyclic hydrocarbon group, an aromatic hydrocarbon group and the like can be mentioned.

As examples of the "alicyclic hydrocarbon group", a monocyclic or fused polycyclic group consisting of 3 to carbon atoms, specifically, a cycloalkyl group, a cycloalkenyl group and a bicyclic or tricyclic fused ring thereof with an aryl group having 6 to 14 carbon atoms (for example, benzene and the like) and the like, and the like can be mentioned. As examples of the "cycloalkyl group", a cycloalkyl group having 3 to 6 carbon atoms, such as cyclopropyl, cyclobutyl, cyclopentyl, cyclohexyl and the like can be mentioned; as examples of the "cycloalkenyl group", a cycloalkenyl group having 3 to 6 carbon atoms, such as cyclopropenyl, cyclobutenyl, cyclopentenyl, cyclohexenyl, and the like can be mentioned.

As examples of the "aromatic hydrocarbon group", a monocyclic aromatic hydrocarbon group consisting of 6 to 18 carbon atoms and a fused polycyclic aromatic hydrocarbon group can be mentioned; specifically, an aryl group having 6 to 14 carbon atoms, such as phenyl, 1-naphthyl, 2-naphthyl, 2-indenyl, 2-anthryl and the like, can be mentioned.

As used herein, "a saturated or unsaturated heterocyclic group" is, for example, a 5- or 6-membered monocyclic group comprising one to two nitrogen atoms, a 5- or 6-membered monocyclic group comprising one or two nitrogen atoms and one oxygen atom or one sulfur atom, a 5-membered monocyclic group comprising one oxygen atom or one sulfur atom, a bicyclic group comprising one to four nitrogen atoms and resulting from the condensation of a 6-membered ring and a 5- or 6-membered ring, and the like; specifically, for example, pyridyl, thienyl, oxadiazolyl, imidazolyl, thiazolyl, isothiazolyl, oxazolyl, isooxazolyl, furyl, pyrrolyl, quinolyl, quinazolinyl, purinyl, pyrazolyl, thiophenyl and the like can be mentioned.

The substituent for "an optionally substituted saturated or unsaturated cyclic hydrocarbon group or saturated or unsaturated heterocyclic group" is not subject to limitation; for example, a saturated or unsaturated cyclic hydrocarbon group (having the same definition as described above), a saturated or unsaturated heterocyclic group (having the same definition as described above), a halogen atom (described below), a carboxyl group, a substituted amido group (described below), an optionally substituted lower alkyl group (described below) and the like can be mentioned. These substituents substitute on the cyclic hydrocarbon group or heterocyclic group, as long as the substitution is chemically acceptable. However, provided that the number of substituents is two or more, they may be identical or not. Preferably, there are two substituents: one substituent selected from the group consisting of optionally substituted, saturated or unsaturated cyclic hydrocarbon group (having the same definition as described above) and an optionally substituted, saturated or unsaturated heterocyclic group (having the same definition as described above) (for example, methylphenyl), and one substituent selected from the group consisting of a halogen atom (described below), a carboxyl group, a substituted amido group (described below) and an optionally substituted lower alkyl group (described below) (for example, trifluoromethyl).

As examples of the "halogen atom", fluorine, chlorine, bromine, iodine and the like can be mentioned.

As the "substituted amido group", an N-substituted amido group or an N,N'-di-substituted amido group can be mentioned; specifically, amido groups substituted by a lower alkyl group (described below) and the like can be mentioned.

As used herein, "a lower alkyl group" represents, for example, a linear, branched or cyclic alkyl group having 1 to 6 carbon atoms; specifically, methyl, ethyl, n-propyl, isopropyl, butyl, isobutyl, sec-butyl, tert-butyl, pentyl, hexyl, cyclopropyl, cyclobutyl and the like can be mentioned. As the "substituent" in "an optionally substituted lower alkyl group", a carboxyl group, a substituted amido group (having the same definition as described above), a cyano group, a halogen atom (having the same definition as described above) and the like can be mentioned.

The 1 to 4 substituents that the benzene ring B optionally has are not subject to limitation, as long as the compound retains bindability to KSRP, and/or is capable of regulating the expression of KSRP and regulating the activity of KSRP, and they may be the same or different. For example, they are saturated or unsaturated hydrocarbon groups (described below) or saturated or unsaturated heterocyclic groups (having the same definition as described above).

As used herein, as "an aryl group", the same examples as those of the aforementioned "aromatic hydrocarbon group" can be mentioned. The "substituent" in "an optionally substituted aryl group" is not subject to limitation; for example, a saturated or unsaturated cyclic hydrocarbon group (having the same definition as described above), a saturated or unsaturated heterocyclic group (having the same definition as described above), a halogen atom (having the same definition as described above), an amino group, a carboxyl group, a substituted amido group (having the same definition as described above), an optionally substituted lower alkyl group (having the same definition as described above) and the like can be mentioned.

As the "substituent" in "an optionally substituted amino group", a lower alkyl group (having the same definition as described above), a lower alkanoyl group (for example, an alkanoyl group having 1 to 6 carbon atoms, such as formyl, acetyl, and propionyl) and the like can be mentioned.

As "a saturated or unsaturated hydrocarbon group", a saturated or unsaturated chain hydrocarbon group or a saturated or unsaturated cyclic hydrocarbon group (having the same definition as described above) and the like can be mentioned.

As examples of "a saturated or unsaturated chain hydrocarbon group", a linear or branched chain hydrocarbon group having 1 to 10 carbon atoms and the like can be mentioned; specifically, for example, an alkyl group, an alkenyl group, an alkynyl group and the like can be mentioned. Of these groups, an alkyl group is particularly preferable. As examples of the "alkyl group", an alkyl group having 1 to 10 carbon atoms such as methyl, ethyl, n-propyl, isopropyl, butyl, isobutyl, sec-butyl, tert-butyl, n-pentyl, isopentyl, neopentyl, n-hexyl, isohexyl and the like can be mentioned. As examples of the "alkenyl group", an alkenyl group having 2 to 10 carbon atoms such as vinyl, 1-propenyl, allyl, isopropenyl, 1-butenyl, 2-butenyl, 3-butenyl, isobutenyl, sec-butenyl and the like can be mentioned. As examples of the "alkynyl group", an alkynyl group having 2 to 10 carbon atoms such as ethynyl, 1-propynyl, propargyl and the like can be mentioned.

The ring that $R_3$ and $R_4$ may bind together to form is specifically a saturated or unsaturated cyclic hydrocarbon group (having the same definition as described above) or a saturated or unsaturated heterocyclic group (having the same definition as described above); this ring is optionally substituted by a halogen atom (having the same definition as described above), a carboxyl group, a substituted amido group (having the same definition as described above), an optionally substituted lower alkyl group (having the same definition as described above) and the like.

The compound of the present invention, represented by the formula (I) or the formula (II), can be produced using various known methods of synthesis by means of the characteristics based on the basic skeleton thereof or the kind of substituent. For example, alkylation, acylation, amination, imination, halogenization, reduction, oxidation, condensation and the like can be mentioned, and reactions or methods in common use in the art can be utilized.

A compound capable of binding to KSRP or a functional fragment thereof, such as the compound of the present invention, represented by the formula (I) or the formula (II), exhibits superior anticancer effect, anti-inflammatory effect and/or brain dysfunction improving effect in mammals such as monkeys, horses, bovines, sheep, dogs, cats, rabbits, mice, rats, and guinea pigs, including humans, and is therefore useful as a therapeutic agent for a proliferative disease such as an anticancer agent, a therapeutic agent for an inflammatory disease and a therapeutic agent for an encephalopathy. Target diseases are as described above.

Spnal, which likewise is capable of binding to KSRP or a functional fragment thereof, also exhibits superior anticancer effect, anti-inflammatory effect and/or brain dysfunction improving effect on various mammals, and is therefore useful as a therapeutic agent for a proliferative disease such as a anticancer agent, a therapeutic agent for an inflammatory disease and a therapeutic agent for an encephalopathy (target diseases are as described above). Spnal is particularly suitable as an anticancer agent.

Compounds represented by the formula (I) or the formula (II), Spnal, and other compounds capable of binding to KSRP or a functional fragment thereof are hereinafter sometimes generically referred to as the compound of the present invention.

The compound of the present invention may have formed a pharmaceutically acceptable salt; as the salt, acid addition salts, for example, inorganic acid salts (for example, hydrochlorides, sulfates, hydrobromides, phosphates and the like), organic acid salts (for example, acetates, trifluoroacetates, succinates, malates, fumarates, propionates, citrates, tartrates, lactates, oxalates, methanesulfonates, p-toluenesulfonates and the like) and the like can be mentioned.

Note that the compound of the present invention or a salt thereof may be a solvate such as a hydrate and the like.

When the compound of the present invention is used as a therapeutic drug for a disease selected from the group consisting of a proliferative disease, an inflammatory disease and an encephalopathy, it is prepared as an ordinary pharmaceutical preparation and administered orally or parenterally.

For oral administration, the compound of the present invention can be administered in a dosage form in common use in the art. For parenteral administration, the compound of the present invention can be administered in a dosage form such as a topical preparation (transdermal agent and the like), a rectal preparation, an injection, or a transnasal agent.

As examples of the oral preparation or rectal preparation, capsules, tablets, pills, powders, drops, cachets, suppositories, liquids and the like can be mentioned. As examples of the injection, a sterile solution or suspension and the like can be mentioned. As examples of the topical preparation, creams, ointments, lotions, transdermal agents (ordinary patches, matrices) and the like can be mentioned.

The above-described dosage forms can be formulated along with a pharmaceutically acceptable excipient and additive by a technique commonly performed in the art. As the pharmaceutically acceptable excipient and additive, carriers, binders, flavoring agents, buffering agents, thickeners, colorants, stabilizers, emulsifiers, dispersing agents, suspending agents, antiseptics and the like can be mentioned.

As examples of pharmaceutically acceptable carriers, magnesium carbonate, magnesium stearate, talc, sugar, lactose, pectin, dextrin, starch, gelatin, gum tragacanth, methylcellulose, sodium carboxymethylcellulose, low-melting wax, cacao butter and the like can be mentioned.

Furthermore, the tablets can be prepared as tablets with ordinary coatings, for example, sugar-coated tablets, enteric coated tablets, film-coated tablets, and two-layer tablets or multi-layer tablets if necessary. The powders are formulated into preparations along with a pharmaceutically acceptable base for powders. As the base, talc, lactose, starch and the like can be mentioned. The drops can be formulated into preparations along with an aqueous or non-aqueous base and one kind or more of pharmaceutically acceptable diffusing agents, suspending agents, solubilizers and the like. The capsules can be produced by filling therein an active ingredient compound, along with a pharmaceutically acceptable carrier. The compound can be filled in the capsules as mixed with a pharmaceutically acceptable excipient, or without an excipient. The cachets can also be produced in the same manner. When the present invention is prepared as a suppository, it is formulated into preparations along with a base such as a vegetable oil (castor oil, olive oil, peanut oil and the like) or a mineral oil (petrolatum, white petrolatum and the like), a wax, or a partially synthesized or totally synthesized glycerine fatty acid ester by a commonly used technique.

As the liquid for injection, solutions, suspensions, emulsions and the like can be mentioned. For example, aqueous solutions, water-propylene glycol solutions and the like can be mentioned. The liquid can also be produced in the form of a solution of polyethylene glycol and/or propylene glycol that may contain water.

A liquid suitable for oral administration can be produced by adding an active ingredient compound to water, and, if required, adding a colorant, flavoring agent, stabilizer, sweetener, solubilizer, thickener and the like. A liquid suitable for oral administration can also be produced by adding the compound, along with a dispersing agent, to water, to increase the viscosity. As examples of the thickener, pharmaceutically acceptable natural or synthetic gums, resins, methylcellulose, sodium carboxymethylcellulose, known suspending agents and the like can be mentioned.

As the topical preparation, the above-described liquids, as well as creams, aerosols, sprays, powders, lotions, ointments and the like can be mentioned. The above-described topical preparation can be produced by mixing an active ingredient compound and a pharmaceutically acceptable diluent and carrier. Ointments and creams are formulated into preparations by, for example, adding a thickener and/or a gelling agent to an aqueous or oily base. As examples of the, base, water, liquid paraffin, vegetable oils and the like can be mentioned. As examples of the thickener, soft paraffin, aluminum stearate, cetostearyl alcohol, propylene glycol, polyethylene glycol, lanolin, hydrogenated lanolin, beeswax and the like can be mentioned. To the topical preparation, an antiseptic such as methyl hydroxybenzoate, propyl hydroxybenzoate, chlorocresol, benzalkonium chloride and the like, and a bacterial growth inhibitor can be added as necessary. A lotion can be prepared by adding one kind or more of pharmaceutically acceptable stabilizers, suspending agents, emulsifiers, diffusing agents, thickeners, colorants, flavoring agents and the like to an aqueous or oily base.

Dosage and frequency of administration vary depending on the kind of compound used, patient symptoms, age, body weight, dosage form and the like, and are set as appropriate according thereto.

The present invention also enables screening for a compound useful in the treatment of various diseases mediated by KSRP, for example, proliferative diseases, inflammatory diseases, and encephalopathies, with specific bindability to KSRP or a functional fragment thereof (the definitions for the individual terms are as described above) as an index. Here, KSRP or a functional fragment thereof can be used as a purified or unpurified protein (polypeptide) or a (functional) fragment thereof, and can be used in a state expressed in cells. KSRP or a (functional) fragment thereof can be acquired by using as appropriate a known technique such as (1) a method comprising isolation and purification from, as a raw material, a culture of cells or a tissue that produces the same, (2) a method comprising chemical synthesis, or (3) a method comprising purification from cells manipulated by gene recombination technology and the like to express KSRP or a (functional) fragment thereof.

Isolation and purification of the KSRP of the present invention or a (functional) fragment thereof can, for example, be performed as described below. That is, KSRP of the present invention or a (functional) fragment thereof is extracted and purified from a tissue expressing the KSRP or a (functional) fragment thereof, or a culture obtained by cultivating cells expressing the KSRP or a (functional) fragment thereof in an appropriate liquid medium, by a known method. For extraction and purification, known methods are used as appropriate depending on the fraction wherein the desired product is present.

Specifically, the extraction and purification are performed as described below. First, the tissue or culture is subjected to a conventional method such as filtration or centrifugation as is, and the tissue or cells or the supernatant is collected. If the desired protein has been accumulated in the cells, the collected cells are suspended in an appropriate buffer agent, and further a surfactant is added at an appropriate concentration to solubilize the membrane. As the surfactant, sodium dodecyl sulfate (SDS), cetyltrimethylammonium bromide (CTAB) and the like can be mentioned; because these exhibit potent protein denaturative effect, it is preferable to use a gently acting nonionic surfactant, for example, Triton X-100 and the like, to ensure that the protein is folded so that it possesses biological activity. Next, the crude extract obtained is treated in the presence of a surfactant if required, using commonly used methods in combination as appropriate to isolate and purify the protein or a functional fragment thereof. As such methods, methods based on solubility, such as salting-out and solvent precipitation; methods based on differences in molecular weight, such as dialysis, ultrafiltration, gel filtration, and SDS-PAGE; methods based on electric charge, such as ion exchange chromatography; methods based on specific affinity, such as affinity chromatography; methods based on differences in hydrophobicity, such as reverse phase high performance liquid chromatography; methods based on differences in isoelectric point, such as isoelectric focusing and the like can be mentioned. More specifically, the protein or a functional fragment thereof can be separated and purified by commonly used methods, for example, concentration under reduced pressure, freeze-drying, extraction with conventionally used solvents, pH adjustment, treatment with conventionally used adsorbents such as anion exchange resin or cation exchange resin, and nonionic adsorbent resin, crystallization, recrystallization and the like.

Production of the KSRP of the present invention or a (functional) fragment thereof by chemical synthesis can be performed by, for example, synthesis or semi-synthesis based on the amino acid sequence information shown by SEQ ID NO:2 or 3 using a peptide synthesizer.

Also, when the KSRP or a (functional) fragment thereof is acquired from cells manipulated to express the same by gene recombination technology and the like, the specific procedures shown below are followed.

First, an expression vector that functionally carries the gene encoding the KSRP or a functional fragment thereof is prepared.

The gene encoding the KSRP or a functional fragment thereof may be obtained from any method. For example, a complementary DNA (cDNA) prepared from an mRNA, a genomic DNA prepared from a genomic library, a chemically synthesized DNA, a DNA obtained by amplification by the PCR method with an RNA or DNA as a template, and a DNA constructed by appropriately combining these methods, and the like are included. For example, a DNA comprising all or a portion of a DNA substantially comprising the base sequence shown by SEQ ID NO:1 (accession No. NM_003685), a DNA comprising all or a portion of a DNA substantially comprising the base numbers 472 to 2226 of SEQ ID NO:1, and the like can be mentioned.

As used herein, "a DNA substantially comprising" means, in addition to the above-described DNAs comprising a particular base sequence, a DNA comprising a base sequence capable of hybridizing to the above-described DNAs comprising a particular base sequence under stringent conditions (in the present invention, these conditions refer to conditions under which a DNA having a homology of about 60% or more, preferably about 80% or more, and more preferably about 90% or more, can hybridize; stringency can be controlled by changing the temperature, salt concentration and the like as appropriate during the hybridization reaction and washing). Stringent conditions can be calculated on the basis of the desired homology, the length of oligonucleotide and the like by applying them to appropriate calculation formulas utilized in the art. For example, hybridization at 42° C. and washing treatment at 42° C. with a buffer solution containing 1×SSC and 0.1% SDS, hybridization at 65° C. and washing treatment at 65° C. with a buffer solution containing 0.1×SSC and 0.1% SDS, and the like can be mentioned.

An expression vector that functionally comprises a gene encoding KSRP or a functional fragment thereof can be obtained by inserting the DNA obtained into a plasmid vector, phage vector and the like capable of retaining replication or autonomous replication in various hosts such as prokaryotic cells and/or eukaryotic cells by means of an appropriate restriction enzyme site.

As used herein, "functionally" means that the gene (DNA) is transcribed in a host cell matching with the vector, and that the gene is arranged to allow the production of the protein encoded thereby. Preferably, the expression vector is a vector having an expression cassette wherein a promoter region, an initiation codon, a gene encoding KSRP or a functional fragment thereof, a stop codon and a terminator region are continuously arranged. For transformant selection, it is preferable that a selection marker gene be further contained.

For example, when a mammalian cell is transformed, a plasmid comprising a promoter of an animal virus, for example, SV40, RSV, MMLV and the like, and a polyadenylation signal, joined to each other via a restriction enzyme site, preferably a multicloning site, wherein a selection marker gene derived from a plasmid such as pSV2-neo or pSV2-dhfr (neomycin resistance gene, dihydrofolate reductase and the like) has been inserted, can be used.

The host cell is not subject to limitation, as long as it matches with the expression vector used, and is transformable; various cells in common use in the technical field of the present invention, such as natural cells or an artificially established recombinant cells and the like, can be utilized. Specifically, bacteria such as *Escherichia coli* and *Bacillus subtilis*, fungi such as yeast, animal cells or insect cells and the like can be mentioned as examples. Preferably, mammalian cells, particularly rat-derived cells, hamster-derived cells (CHO, BHK and the like), mouse-derived cells (COP, L, C127, Sp2/0, NS-1, NIH T3 and the like), monkey-derived cells (COS1, COS3, COS7, CV1, Velo and the like) and human-derived cells (Hela, diploid fibroblast-derived cells, myeloma cells, Namalwa, Jurkat cells and the like) can be mentioned.

Introduction of an expression vector to a host cell can be performed using a conventionally known method. For example, when the expression vector is introduced to a mammalian cell, the calcium phosphate co-precipitation method, the protoplast fusion method, the microinjection method, the electroporation method, the lysosome method and the like can be mentioned.

KSRP or a functional fragment thereof can also be produced by cultivating a transformant comprising an expression vector prepared as described above. The medium preferably contains a carbon source and an inorganic or organic nitrogen source required for the growth of the host cell (transformant). As examples of the carbon source, glucose, dextrin, soluble starch, sucrose and the like can be mentioned; as examples of the nitrogen source, ammonium salts, nitrates, amino acids, corn steep liquor, peptone, casein, meat extract, soybean cake, potato extract and the like can be mentioned. If desired, other nutrients [for example, inorganic salts (calcium chloride, sodium dihydrogen phosphate, magnesium chloride and the like), vitamins, antibiotics (tetracycline, neomycin, kanamycin, ampicillin and the like)] may be contained.

The cultivation is performed by a method known in the art. The cultivation conditions are conditions enabling the expression of the protein; for example, temperature, medium pH and cultivation time are chosen as appropriate so that the protein is produced in a large amount.

For example, when the host is an animal cell, as examples of the medium, a minimal essential medium (MEM) supplemented with about 5 to 20% fetal calf serum (FCS), Dulbecco's modified Eagle medium (DMEM), RPMI-1640 medium, 199 medium and the like can be used. The pH of the medium is preferably about 6 to 8, the cultivation is normally performed at 30 to 40° C. for about 15 to 72 hours, and the culture may be aerated or agitated as necessary.

The KSRP of the present invention or a functional fragment thereof can be collected from the culture obtained from the above-described cultivation in the same manner as the aforementioned extraction, isolation, and purification from cells or tissue expressing KSRP or a functional fragment thereof.

Contact treatment of the KSRP or a functional fragment thereof thus obtained and a test compound can be performed in accordance with a binding experiment commonly performed in the art. Specifically, the KSRP or a functional fragment thereof or a test compound is immobilized to a solid phase carrier and when the KSRP or a functional fragment thereof is immobilized, a solution comprising the test compound is brought into contact with the solid phase carrier; when a test compound is immobilized to a solid phase carrier, a solution comprising the KSRP or a functional fragment thereof (a purified protein solution or a crudely purified protein solution such as cell extract or tissue extract) is brought into contact with the solid phase carrier. The column method, batch method and the like can be utilized.

The step of determining whether or not the test compound specifically binds to KSRP or a functional fragment thereof can be changed as appropriate depending on how the step of bringing the test compound into contact with KSRP or a functional fragment thereof has been performed; for example, when using a column packed with a solid phase carrier (for example, bead resin) immobilized with the test compound, KSRP molecules bind onto the solid phase carrier by the subsequent addition of a solution (sample) comprising KSRP or a functional fragment thereof, provided that there is specific affinity between the two (do not bind in the absence of specific affinity). It is also possible to dissociate the bound KSRP or a functional fragment thereof from the solid phase by a treatment such as altering the polarity of the buffer solution or further adding the test compound in excess, and then identify the KSRP or a functional fragment thereof, or to extract the KSRP or a functional fragment thereof with a surfactant and the like while remaining in a state bound to the test compound on the solid phase, and then identify the KSRP or a functional fragment thereof. As the method of identification, specifically, known techniques such as electrophoresis, immunoblotting and immunoprecipitation, which employ immunological reactions, chromatography, mass spectrometry, amino acid sequencing, and NMR, or combinations of these methods can be used. By determining whether or not KSRP or a functional fragment thereof is captured onto the solid phase or contained in the column effluent fraction, or the extent thereof and the like, a judgment is made as to whether or not the test compound is capable of specifically binding to KSRP, and a binding compound is selected.

Also, this step may be automated. For example, it is also possible to directly read data of various molecules obtained by two-dimensional electrophoresis, and identify the molecules on the basis of existing databases.

Furthermore, when KSRP or a functional fragment thereof is used in a state expressed in cells, it is also possible to measure the presence or absence of binding of KSRP or a functional fragment thereof and the test compound and the degree of binding by making use of various labeling techniques such as RI labeling and fluorescence labeling. "Contact of KSRP or a functional fragment thereof and the test compound" in the screening method of the present invention also includes this mode. The contact conditions of cells and the test compound are set as appropriate depending on factors such as the cells used and the status of expression of KSRP or a functional fragment thereof in the cells. Also, whether or not KSRP or a functional fragment thereof is expressed in the cells is preferably confirmed in advance using an antibody and the like.

EXAMPLES

The present invention is hereinafter described in more detail by means of the following production examples and example, which examples, however, are not to be construed as limiting the scope of the invention.

Production Example 1

Synthesis of Sulindac-Sulfide-Immobilized Resin (A)

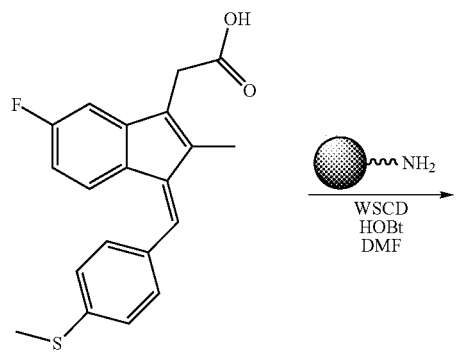

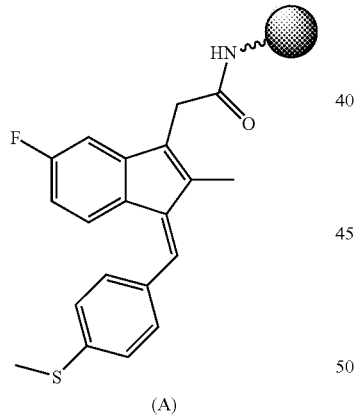

(A)

TOYO-Pearl (AF-Amino-650M) (600 μl, 60 μmol; TOSHO, Cat. NO =08039), sulindac sulfide (20.4 mg, 60 μmol; SIGMA, Cat. NO. =S-3131), WSCD (11.6 μl, 66 μmol; Peptide Institute, Inc., Cat. NP =1020; water-soluble carbodiimide), and HOBt (9.7 mg, 72 μmol; 1-hydroxybenzotriazole) were added, and this was followed by stirring at room temperature for one day. After the resin was washed with DMF (dimethylformamide) five times, the ninhydrin test was performed, showing that the desired compound was obtained with a yield of 93%.

Subsequently, 5 ml of a 20% acetic anhydride solution in DMF was added, and this was followed by stirring at room temperature for 30 minutes, and the remaining amino groups were capped with acetyl groups. The resin was washed with 5 ml of 20% ethanol solution to yield the desired compound (A).

Production Example 2

Synthesis of Sulindac-Immobilized Resin (B)

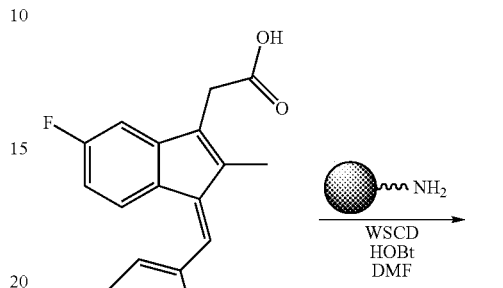

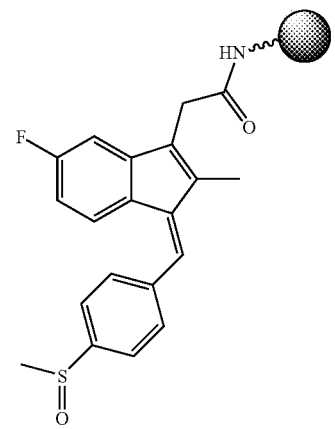

(B)

TOYO-Pearl (AF-Amino) (600 μl, 60 μmol), sulindac (21.4 mg, 60 μmol; SIGMA Cat. NO =S-8139), WSCD (11.6 μl, 66 μmol), and HOBt (9.7 mg, 72 μmol) were added, and this was followed by stirring at room temperature for one day. After the resin was washed with DMF five times, the ninhydrin test was performed, showing that the desired compound was obtained with a yield of 92%.

Subsequently, 5 ml of a 20% acetic anhydride solution in DMF was added, and this was followed by stirring at room temperature for 30 minutes, and the remaining amino groups were capped with acetyl groups. The resin was washed with 5 ml of 20% ethanol solution to yield the desired compound (B).

Production Example 3

Synthesis of Sulindac-Sulfone-Immobilized Resin (C)

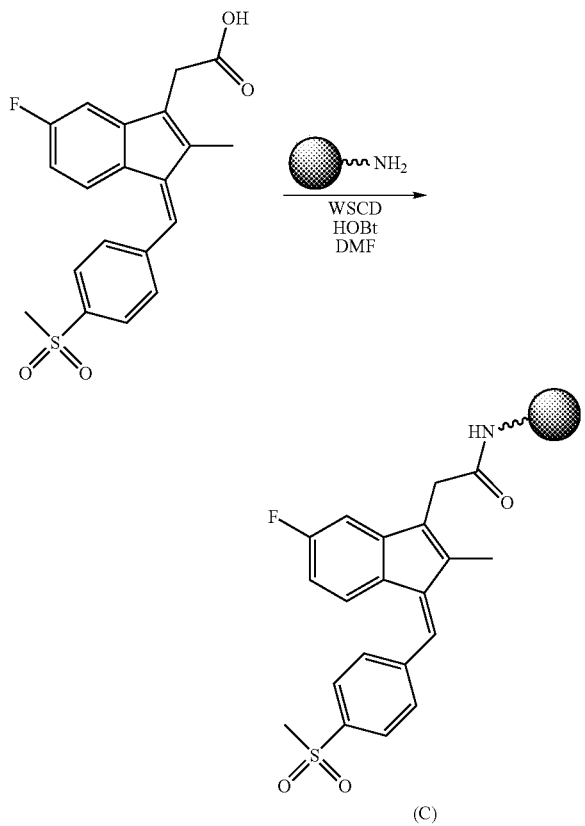

TOYO-Pearl (AF-Amino) (600 μl, 60 μmol), sulindac sulfone (22.3 mg, 60 μmol; SIGMA Cat. NO =S-1438), WSCD (11.6 μl, 66 μmol), and HOBt (9.7 mg, 72 μmol) were added, and this was followed by stirring at room temperature for one day. After the resin was washed with DMF five times, the ninhydrin test was performed, showing that the desired compound was obtained with a yield of 87%.

Subsequently, 5 ml of a 20% acetic anhydride solution in DMF was added, and this was followed by stirring at room temperature for 30 minutes, and the remaining amino groups were capped with acetyl groups. The resin was washed with 5 ml of 20% ethanol solution to yield the desired compound (C).

Production Example 4

Synthesis of Celecoxib-Derivative-Immobilized Resin (D-2)

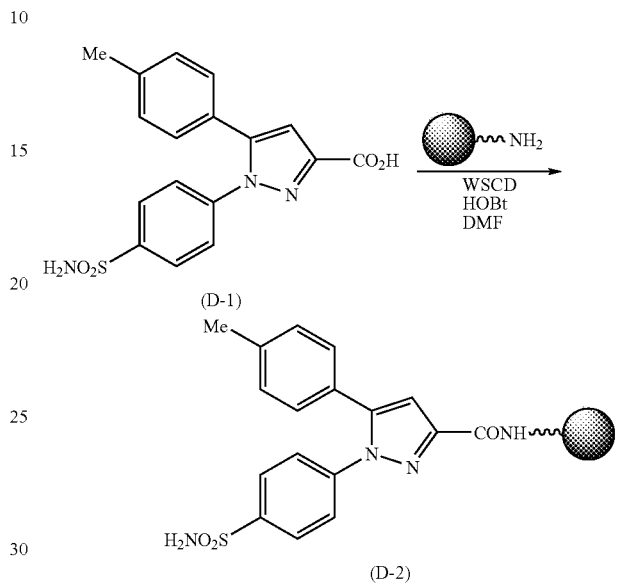

TOYO-Pearl (AF-Amino), compound D-1 (synthesized as described in J. Med. Chem. 1997, 40, 1347-1365) (21.4 mg, 60 μmol), WSCD (11.6 μl, 66 μmol), and HOBt (9.7 mg, 72 μmol) were added, and this was followed by stirring at room temperature for one day. After the resin was washed with DMF five times, the ninhydrin test was performed, showing that the desired compound was obtained with a yield of 92%.

Subsequently, 5 ml of a 20% acetic anhydride solution in DMF was added, and this was followed by stirring at room temperature for 30 minutes, and the remaining amino groups were capped with acetyl groups. The resin was washed with 5 ml of 20% ethanol solution to yield the desired compound (D-2).

Production Example 5

Synthesis of Taxol-Immobilized Resin (E)

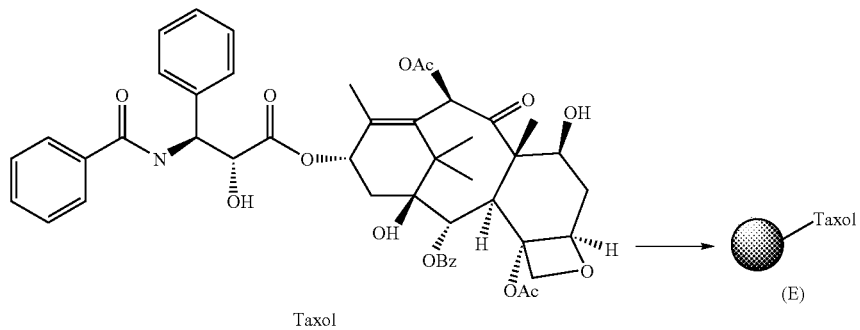

Taxol (35 mg, 41 μmol; WAKO, Cat. NO =163-18614) was dissolved in acetonitrile (2 ml) and cooled to 0° C., after which a phosgene/toluene solution (1.24 mmol/ml, 3.3 ml) and diisopropylethylamine (42 μl, 240 μmol) were added. After the reaction mixture was stirred at room temperature for 1 hour, the solvent was evaporated under reduced pressure. The residue was dissolved in acetonitrile, this solution was added to 100 4l of TOYO-Pearl (TSKgel AF-amino; 0.01 mmol of amine present in 100 μl), diisopropylethylamine (42 μl, 240 μmol) was further added, and this was followed by overnight shaking at room temperature. After completion of the reaction, the resin was thoroughly washed with acetonitrile and distilled water in this order, after which saturated aqueous sodium hydrogen carbonate solution (1.2 ml) was added, and this was followed by shaking at room temperature for 30 minutes; thereafter, the resin was thoroughly washed with distilled water and acetonitrile in this order. By the ninhydrin test, the Taxol introduction rate was determined to be about 75%. To this resin, a mixed solution of acetic anhydride/DMF (1/4) (1.0 ml) was added; this was followed by shaking at room temperature for 30 minutes. After completion of the reaction, the resin was thoroughly washed with DMF and 20% aqueous ethanol solution to yield Taxol-immobilized resin (E).

Example 1

(1-1) Preparation of Rat Brain Lysate

The rat brain (2.4 g) was mixed in a mixture A (25 mM Tris-HCl pH 8.0, 0.5% Tween 20, 300 μM DCC (24 ml; N,N-diethyldithiocarbamate sodium)) and prepared as a homogenate, which was then centrifuged at 9,000 rpm for 10 minutes. The centrifugal supernatant was collected and further centrifuged at 50,000 rpm for 30 minutes. The supernatant thus obtained was used as the lysate.

Note that all experiments were performed at 40° C. or on ice.

(1-2) Binding Experiments

Binding experiments were performed using the immobilizing resins with each test compound immobilized thereon, prepared in Production Examples 1 to 5, and the rat brain lysate prepared in Example 1(1-1), per the procedures shown below.

Each resin (10 μl) and lysate (1 ml) were gently shaken at 4° C. for about 1 hour. Thereafter, centrifugal operation was performed, and each supernatant was collected carefully. Then, each supernatant was again mixed with a fresh compound-bound resin (10 μl). At this time, the separated compound-bound resin was kept to stand at 4° C. as the resin from the first binding experiment. After the mixture was gently stirred for about 3 hours, centrifugal operation was performed, and the supernatant was removed. Subsequently, the compound-bound resin obtained in the second binding experiment and the resin obtained in the first binding experiment were gently washed with mixture A about five times to remove substances other than the protein bound onto the resin to the maximum possible extent. To each compound-bound resin thus obtained, 25 μl of a loading buffer for SDS (nakalai Cat. NO =30566-22, sample buffer solution for electrophoresis with 2-ME (2-mercaptoethanol) (2×) for SDS PAGE) was added; this was followed by stirring at 25° C. for 10 minutes. The sample solution thus obtained was separated using a commercially available SDS gel (BioRad readyGel J, 15% SDS, Cat. NO =161-J341), and the SDS gel was analyzed (FIG. 1). An electrophoresis image of the sample solution comprising a protein bound onto the bound resin obtained in the first binding experiment (denoted as (−) for convenience in FIG. 1, designated) and an electrophoresis image of the sample solution comprising a protein bound onto the bound resin obtained in the second binding experiment (denoted as (+) for convenience in FIG. 1, designated) were compared.

As a result, MARTA1 (a rat protein having a high homology to KSRP; homology =98%; J. Neurochem., 82(5), 1039-46 (2002)) bound to the resins immobilized with four compounds other than the resin immobilized with sulindac sulfide, and the binding was remarkably confirmed in the first binding experiment with the compound-bound resin but minimally observed in the second binding experiment; therefore, the binding was shown to be a specific binding. Note that similar results were obtained when using a human type KSRP protein (partial protein 127-711; SEQ ID NO:3) expressed in host cells.

Because the NSAID derivatives obtained to date have been created by screening with anti-inflammatory action as an index, a compound useful not only for anti-inflammatory effect but also for cancer can be obtained by re-screening with the effect on KSRP, which exhibits behavior more consistent to anticancer effect, as an index.

Preferred embodiments of this invention are described herein, including the best mode known to the inventors for carrying out the invention. It should be understood that the illustrated embodiments are exemplary only, and should not be taken as limiting the scope of the invention. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

The invention claimed is:

1. A compound represented by the formula (I) or the formula (II) or a pharmaceutically acceptable salt thereof:

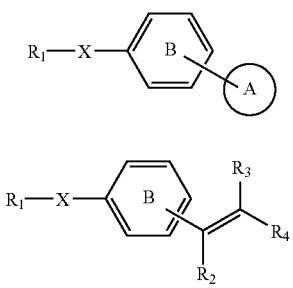

wherein X is

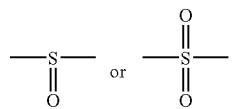

ring A is an optionally substituted saturated or unsaturated cyclic hydrocarbon group or saturated or unsaturated heterocyclic group;

ring B is a benzene ring optionally further having one to four substituents;

$R_1$ is an optionally substituted lower alkyl group, an optionally substituted aryl group, a substituted amido group or an optionally substituted amino group, wherein in the formula (I), when X is —$SO_2$—, $R_1$ is not —$NH_2$—;

each of $R_2$ to $R_4$, whether identical or not, is a hydrogen atom, a saturated or unsaturated hydrocarbon group or a saturated or unsaturated heterocyclic group ($R_3$ and $R_4$ may bind together to form a ring), except that the compounds shown below are excluded

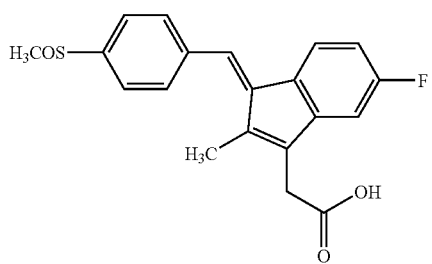

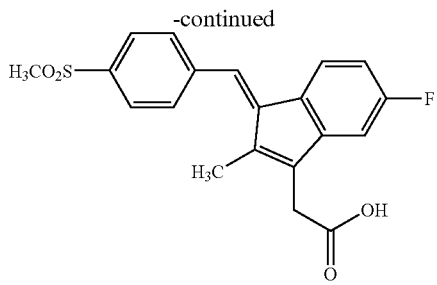

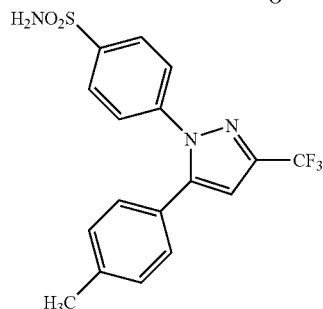

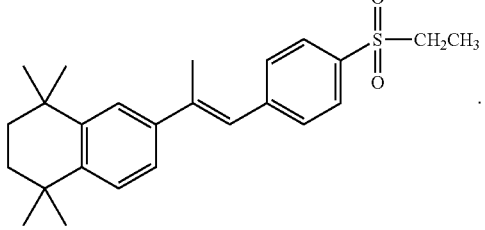

2. The compound of claim 1, wherein the compound represented by the formula (I) is a compound represented by the formula (I'):

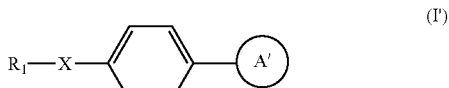

wherein ring A' is an optionally substituted saturated or unsaturated heterocyclic group, and $R_1$ and X are as defined in claim 1, or a pharmaceutically acceptable salt thereof.

3. The compound of claim 2, wherein in the formula (I'), the ring A' is a saturated or unsaturated cyclic hydrocarbon group or saturated or unsaturated heterocyclic group optionally substituted by at least one substituent selected from the group consisting of saturated or unsaturated cyclic hydrocarbon groups, saturated or unsaturated heterocyclic groups, carboxyl groups, substituted amido groups and optionally substituted lower alkyl groups, or a pharmaceutically acceptable salt thereof.

4. The compound of claim 2, wherein in the formula (I'), the ring A' is a saturated or unsaturated heterocyclic group having both any one substituent selected from the group consisting of saturated or unsaturated cyclic hydrocarbon groups and saturated or unsaturated heterocyclic groups, and any one substituent selected from the group consisting of carboxyl groups, substituted amido groups and optionally substituted lower alkyl groups, or a pharmaceutically acceptable salt thereof.

5. The compound of claim 1, wherein in the formula (II), the ring formed by mutually binding $R_3$ and $R_4$ is a saturated or unsaturated cyclic hydrocarbon group or a saturated or unsaturated heterocyclic group optionally having at least one substituent selected from the group consisting of carboxyl groups, substituted amido groups and optionally substituted lower alkyl groups, or a pharmaceutically acceptable salt thereof.

6. The compound of claim 5, wherein in the formula (II), the ring formed by binding of $R_3$ and $R_4$ is a saturated or unsaturated cyclic hydrocarbon group optionally having at least one substituent selected from the group consisting of carboxyl groups, substituted amido groups and optionally substituted lower alkyl groups, or a pharmaceutically acceptable salt thereof.

7. The compound of claim 6, wherein the saturated or unsaturated cyclic hydrocarbon group is indene, or a pharmaceutically acceptable salt thereof.

8. A pharmaceutical composition comprising, as an active ingredient, the compound of claim 1 or a pharmaceutically acceptable salt thereof.

9. The pharmaceutical composition of claim 8, wherein the active ingredient is present in an amount effective to treat a disease selected from the group consisting of a proliferative disease, an inflammatory disease and an encephalopathy.

* * * * *